United States Patent [19]
Breen et al.

[11] Patent Number: 5,859,258
[45] Date of Patent: Jan. 12, 1999

[54] PROCESS FOR THE CRYSTALIZATION OF LOSARTAN

[75] Inventors: Patrick Breen, Dorado, Puerto Rico; Erik A. Dienemann, Metuchen, N.J.; Albert D. Epstein, Edison; Karen A. Larson, Scotch Plains, both of N.J.; Michael T. Kennedy, Goleta, Calif.; Hari Mahadevan, Annadale, N.J.

[73] Assignee: Merck & Company, Inc., Rahway, N.J.

[21] Appl. No.: 959,209

[22] Filed: Oct. 28, 1997

Related U.S. Application Data

[60] Provisional application No. 60/029,326, Oct. 29, 1996.

[51] Int. Cl.$^6$ .................. C07D 257/04; A61K 31/14
[52] U.S. Cl. ............................. 548/252; 514/381
[58] Field of Search ........................ 548/252, 254

[56] References Cited

U.S. PATENT DOCUMENTS

| | | | |
|---|---|---|---|
| 5,130,439 | 7/1992 | Lo et al. | 548/110 |
| 5,138,069 | 8/1992 | Carini et al. | 548/253 |
| 5,206,374 | 4/1993 | Lo | 548/110 |
| 5,310,928 | 5/1994 | Lo et al. | 548/252 |
| 5,608,075 | 3/1997 | Campbell, Jr. et al. | 548/252 |

FOREIGN PATENT DOCUMENTS

| | | |
|---|---|---|
| 93/10106 A1 | 5/1993 | WIPO . |
| 95/17396 | 6/1995 | WIPO . |

*Primary Examiner*—Alan L. Rotman
*Assistant Examiner*—Charanjit S. Aulakh
*Attorney, Agent, or Firm*—Valerie J. Camera; Mark R. Daniel; J. Antonio Garcia-Rivas

[57] ABSTRACT

Losartan potassium is an angiotensin II antagonist useful in the treatment of hypertension and congestive heart failure.

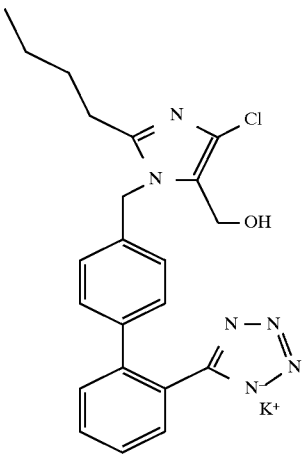

This invention relates to the process for the controlled crystallization of losartan potassium utilizing anti-solvent addition combined with massive seeding in order to obtain the desired crystal morphology and bulk physical properties necessary for successful formulation.

8 Claims, 1 Drawing Sheet

PROCESS FOR THE CRYSTALIZATION OF LOSARTAN

This application is related to provisional patent application U.S. Ser. No. 60/029,326, filed Oct. 29, 1996.

BACKGROUND OF THE INVENTION

Losartan potassium also known as 2-butyl-4-chloro-1-[(2'-tetrazol-5-yl)-biphenyl-4-yl]methyl]-5-(hydroxymethyl) imidazole potassium salt has been approved for the treatment of hypertension.

Losartan is known to inhibit the action of the octapeptide hormone angiotensin II (AII) and is useful therefore in alleviating angiotensin induced hypertension. The enzyme renin acts on a blood plasma $\alpha_2$-globulin, angiotensinogen, to produce angiotensin I, which is then converted by angiotensin converting-enzyme to AII. The latter substance is a powerful vasopressor agent which has been implicated as a causitive agent for producing high blood pressure in various mammalian species, such as the rat, dog, and man. Losartan inhibits the action of AII at its receptors on target cells and thus prevents the increase in blood pressure produced by this hormone-receptor interaction. By administering losartan to a species of mammal with atherosclerosis and/or high cholesterol and/or hypertension due to AII, the blood pressure is reduced. Losartan is also useful for the treatment of high cholesterol by reducing the total cholesterol. Administration of losartan with a diuretic such as furosemide or hydrochlorothiazide, either as a stepwise combined therapy (diuretic first) or as a physical mixture, enhances the antihypertensive effect of losartan, while also treating atherosclerosis and reducing cholesterol levels. Administration of losartan with a non-steroidal anti-inflammatory drug (NSAID) can prevent renal failure which sometimes results from administration of a NSAID.

DETAILED DESCRIPTION OF THE INVENTION

Figure 1:
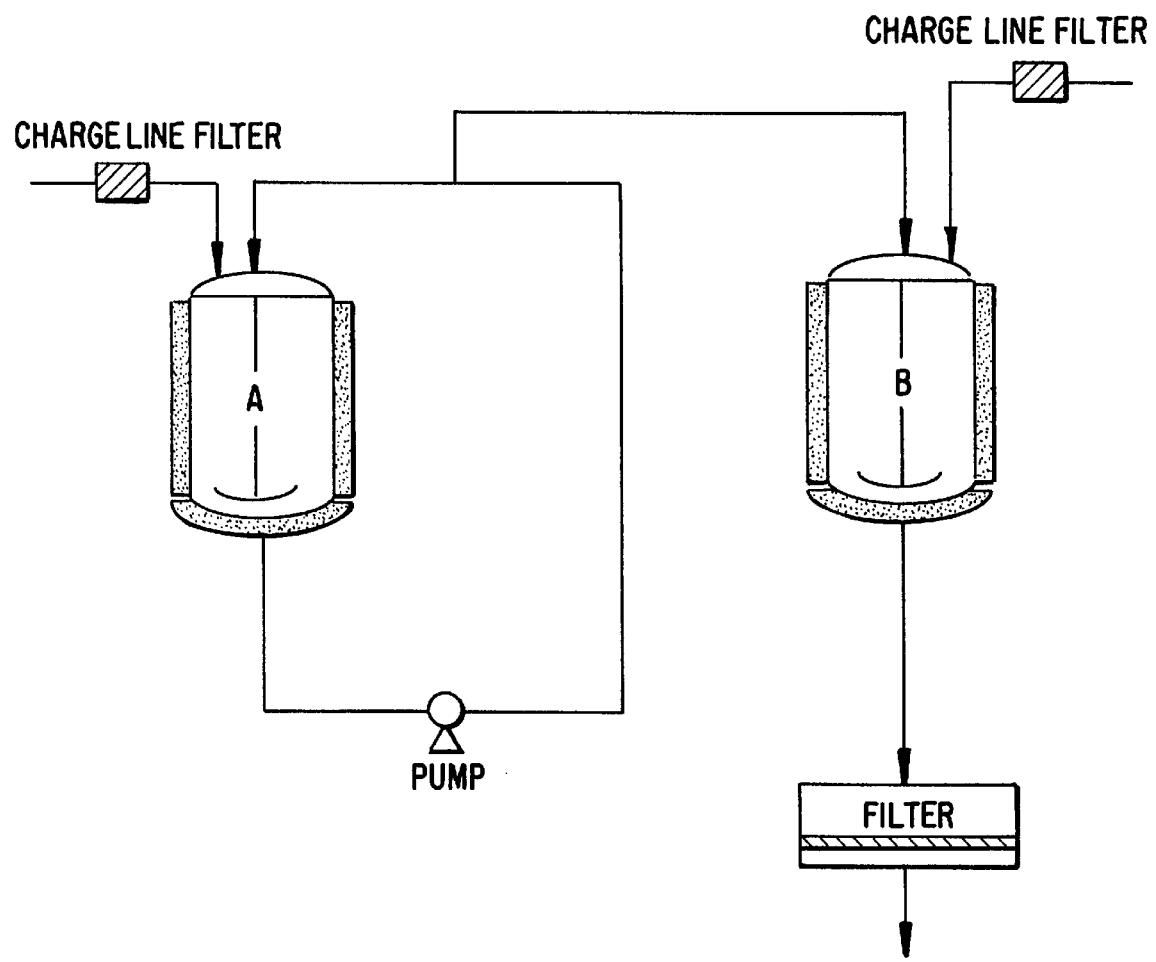
FIG. 1. A schematic of the equipment layout for the crystallization process.

This invention relates to the process for the controlled crystallization of losartan potassium utilizing anti-solvent addition combined with massive seeding in order to obtain the desired crystal morphology and bulk physical properties necessary for successful formulation.

The process for the crystallization of losartan potassium comprising the steps of:

a) distilling an isopropanol-water mixture containing losartan potassium to about 2.4 to about 2.8% water content;

b) cooling the mixture to between about 65° and about 70° C.;

c) adding about a 0.5% by weight finely-milled losartan potassium in cyclohexane slurry at between about 60° and about 65° C. at a rate of about 0.3 l/min. to the vessel until the cloud point is reached at about 1.8 to about 2.3% water content;

d) aging the mixture for about ten minutes;

e) adding about 3 to about 10% by weight finely-milled losartan potassium to seed the mixture at a temperature range of about 60° C. to about 70° C.;

f) aging the seeded mixture for about 1 to about 2 hours at a temperature range of about 60° C. to reflux while stirring;

g) adding about a 60°–65° C. solution of cyclohexane over about a two hour period maintaining a temperature of about 68° C. for the mixture;

h) distilling the mixture at a constant volume to a water content of about 0.5%, while maintaining the constant volume by addition of between about a 50:50 and a 80:20 volume to volume ratio of cyclohexane and isopropanol;

i) distilling the mixture to a slurry density of about 200 g/l and a water content of about less than 0.1%, while adding cyclohexane to maintain about a volume to volume ratio of between about a 50:50 to about a 60:40 cyclohexane: isopropanol, if necessary;

j) cooling the mixture to between about 20° C. and about 30° C.;

k) filtering the mixture to isolate the crystalline losartan potassium;

l) washing the crystalline material with 75:25 cyclohexane: isopropanol;

m) washing the crystalline material with cyclohexane; and n) drying the crystalline losartan potassium under vacuum at a temperature of about 45° to about 50° C.

An embodiment of the process as recited above wherein about 3 to about 8% by weight finely-milled losartan potassium seed is added.

An embodiment of the process as recited above wherein the the isopropanol-water distillation step is run until about 2.6 to about 2.8% water content is reached.

An embodiment of the process as recited above wherein the cyclohexane-losartan potassium slurry until the cloud point is reached at about 1.8 to about 2.0% water content.

An embodiment of the process as recited above wherein the temperature during the seed step is about 65° to about 70° C.

An embodiment of the process as recited above wherein the constant volume distillation is conducted until the water content is less than 0.5%.

A preferred embodiment of the process as recited above wherein about 5% by weight finely-milled losartan potassium seed is added.

An embodiment of the process as recited above wherein the particle size of the finely-milled losartan potassium seed is about 8 to about 10 µm.

Losartan is well known as 2-butyl-4-chloro-1-[(2'-tetrazol-5-yl)-biphenyl-4-yl]methyl]-5-(hydroxy-methyl) imidazole potassium salt (Formula I) has been shown to be useful in the treatment of hypertension as an $AT_1$ selective angiotensin II antagonist.

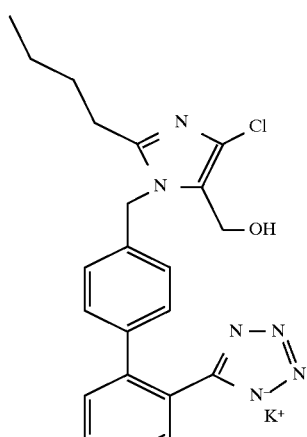

Losartan potassium

Losartan potassium may be prepared using the reactions and techniques described in U.S. Pat. No. 5,138,069 and WO 93/10106 or one of its three U.S. counterparts, U.S. Pat. No. 5,130,439 issued Jul. 14, 1992, U.S. Pat No. 5,206,374 issued Apr. 27, 1993, and U.S. Pat. No. 5,310,928 issued May 10, 1994. The above losartan references are hereby incorporated by reference.

The losartan potassium formulation process was developed using material that was crystallized via nucleation using an uncontrolled, distillation process. The crystal morphology was that of small, flat rods. In an attempt to put more control into the existing crystallization procedure, the "distillative" process was refined somewhat to include seeding and maintenance of constant solvent composition. However, the resultant morphology was that of large 3-D clusters. This material could not be formulated using the existing formulation process. Experiments comparing the formulation properties of small, flat rods produced by a different experimental crystallization process, with that of the clusters, proved conclusively the importance of crystal size and morphology in the formulation. This resulted in strict particle size and bulk density specifications on bulk losartan potassium.

Use of an anti-solvent-controlled seeding process evolved from our prior work and the need to make improvements. Cyclohexane as the antisolvent rather than distillation was used as the main driving force for crystallization. This allows for more control over the approach to saturation than distillation. (Cyclohexane is used as an antisolvent. Seed in the cyclohexane was used, but not for the purpose of determining the cloud point). However, use of antisolvent alone or with some seed in it still resulted in variable physical properties because of the tendency for the K-salt to supersaturate and then spontaneously nucleate. Refinements to this process included tighter temperature control, tighter control over the water content, and the massive seed dose at saturation. This was the point at which the process was able to produce crystals having the desired particle size distribution and morphology needed for successful formulation.

The current process utilized the more traditional concept of crystallization, that is, use of antisolvent addition to control the approach to saturation and to control crystal growth. In this process, the losartan potassium salt, isopropanol:water solution is distilled to a KF of about 2.6%. Cyclohexane containing a small amount of seed (0.5% seed is 5% by weight in solution of the anticipated K-salt product, which is 5% of the amount expected from the crystallization) is added until the onset of crystallization, termed "cloud point". The seed is added to the cyclohexane to help prevent supersaturation of the batch. Thus, the seed will dissolve during the inital stages of the cyclohexane addition, but as the batch approaches saturation, the seed will not dissolve, and the batch will appear cloudy. During some of the runs, interpretation of the cloud point was difficult. Some batches appeared cloudy at a KF of about 2.4%. When this batch was seeded at a KF of 2.25%, the seed dissolved. Thus, cloud point alone cannot be used as the sole interpretation of the saturation point. As more experience was gained with the process, KF ranges were tightened, thus minimizing the need to interpret a cloud point. Rather, the 5% seed charge was made based on a KF after a given amount of cyclohexane slurry had been added. Thus, when enough cyclohexane/seed had been added to reduce the batch KF to about 1.8 to about 2.0%, the batch was seeded with 5% finely-milled seed. In previous processes, use of finely-milled seed resulted in formation of clusters. In this process, an "annealing" age was introduced after the seed addition, whereby, stress points induced in the crystal as a result of milling, are relieved by the dynamic solubility equilibrium of the system. At the end of the age, the rest of the cyclohexane is added, slowly to the batch to bring the cyclohexane:isopropanol volume to volume ratio to about 55:45. At this point, processing continues as with the all-distillation process. The advantage, however, is that the KF is much lower (1.2 to 1.3% vs. 1.5 to 1.6%) so that more batch has crystallized. In fact, roughly 50% of the batch has crystallized at this KF. Consequently, the distillation time cycle becomes a less critical factor in nucleation and crystal growth.

| Flow Diagram of Crystallization Process | |
|---|---|
| I) Cyclohexane Slurry Preparation Vessel A | II) Drying & Crystallization Vessel B |
| 1) Charge 12.4 kg Cyclohexane (CH) | 5) Charge 25.4 kg isopropanol (IPA) |
| 2) Charge 40 g losartan potassium (K-salt) | 6) Charge 900 ml water |
| 3) Heat to 60° C. | 7) Charge 8.0 kg K-Salt |
| 4) Recycle slurry | 8) Distill to about 2.6% water content (maintaining a constant volume) |
| 9a) Transfer slurry to cloud pt. (about 1.9% water content) | 9b) Age 10 min. |
| 12) Charge 19 kg CH and heat to 60° C. | 10) Seed with 400 g finely-milled K-salt |
| 13) Transfer CH over 1 hour | 11) Age 2 hrs at 68° C. |
| | 14) Distill to about 0.5% water content, adding back 75:25 CH:IPA |
| | 15) Concentrate to 200 g/l |
| | 16) Cool to ~25° C. |
| | 17) Sample for KF, LC, GC |
| | 18) Drop to 19" filter pot |
| | 19) Wash with 20 kg of 75:25 CH:IPA |
| | 20) Wash with 20 kg of CH |
| | 21) To vacuum dryer, milling & blending |

The following examples further illustrate the preparation of losartan potassium and, as such, are not to be considered or construed as limiting the invention recited in the appended claims.

EXAMPLE 1

2-n-butyl-4-chloro-1-[(2'-(tetrazol-5-yl)- 1,1'-biphenyl-4-yl)-methyl]-1H-imidazole-5-methanol potassium salt Isopropanol (23.4 kg) was charged to a 50 gallon vessel, followed by 7.5 kg of 2-n-butyl-4-chloro-1-[(2'-(tetrazol-5- yl)-1,1'-biphenyl-4-yl)-methyl]-1H-imidazole-5-methanol free acid (98.6 wt % purity). The batch was heated to 35°–45° C., and 1.864 kg of 8.91N KOH was added followed by a one hour age.

80 ml of 8.91N KOH was added, and after a 15 minute age, the free acid content was reduced to 2.02%. Finally, 35 ml of KOH brought the residual free acid level to 0.1% (99.9% conversion to potassium salt). The batch was transferred into a poly drum using 7–15 psi nitrogen pressure. The original 50 gallon vessel was rinsed with 5 gal of cyclohexane:isopropanol that was discarded, and the batch was recharged to the vessel through a 10 μm followed by a 0.6 μm filter using residual vacuum.

The batch was distilled at constant volume with concomitant addition of isopropanol to reduce the water content. A total of 21.5 l was distilled. [The distillation temperature was 82° C. The batch KF was 2.56%; 30 ml of water was added to bring the KF up to 2.64%. KF refers to a Karl Fischer titration which analyzes for water content.]

During the isopropanol distillation, 12.4 kg of cyclohexane and 40 g of finely-milled K-salt was charged to a 20 gallon vessel and heated to 60°–65° C. The slurry was then recycled around in the 20 gal. vessel in preparation for transfer to the 50 gallon crystallizer. When the transfer was started, it was noted that the K-salt solution was clear. The rate of transfer was approximately 0.3 L/min. The temperature in 20 gal. vessel was 55°–60° C. while that of the 50 gallon vessel was 65°–74° C. A total of 10.6 kg of slurry was needed to reach the cloud point (the KF of the batch was 1.94%). The amount of slurry added was determined by emptying 20 gal. vessel and weighing the remaining material. By gas chromatography, the cyclohexane/isopropanol volume/volume ratio was 25/75.

Four hundred grams of finely-milled K-salt was charged to the batch and aged at 68° C. for two hours.

Cyclohexane (20.5 kg) was charged to the 20 gal. vessel and heated to 60°–65° C. This material was charged to the 50 gal. vessel using nitrogen pressure over a period of two hours while maintaining the batch temperature at 68° C.

The batch was distilled at constant volume with concomitant addition of 75:25 cyclohexane:isopropanol. A total of 57 liters was distilled, and 45 kg of 75:25 added.

The batch was concentrated to a volume of about 38 liters by distilling 47.3 liters and charging back 6.0 kg of cyclohexane. By gas chromatography, the cyclohexane/isopropanol volume/volume ratio was 64.6:35.4.

An additional 22.7 liters of distillate was collected while simultaneously adding 18 kg of 75:25 cyclohexane:isopropanol to reduce the final batch KF to 0.02%. The K-salt concentration was 2.3 g/l.

The batch was then cooled to 20°–30° C. and filtered on a 19" filter pot lined with cloth/paper/cloth, and washed with 20 kg 75:25 cyclohexane:isopropanol followed by 20 kg of cyclohexane. The batch was dried on trays under vacuum with a 0.5 SCFM nitrogen sweep at 45°–50° C. for 8 hours. A total of 7.6 kg was produced having an HPLC wt % purity of 99.9%.

EXAMPLE 2
2-n-butyl-4-chloro-1-[(2'-(tetrazol-5-yl)-1,1'-biphenyl-4-yl)-methyl]-1H-imidazole-5-methanol potassium salt 25.4 kg of isopropanol and 8.0 kg of K-salt were charged to a 50 gallon vessel along with 930 ml of DI water. The KF of the dissolved solution was 2.48%. In a 20 gallon vessel, 12.4 kg of cyclohexane and 40 g of K-salt milled seed was heated to 60°–65° C. and added to the 50 gallon vessel over a period of 40 minutes until the solution became cloudy. During this addition, the contents of a 50 gallon vessel were maintained at reflux (the reflux temperature decreased from 74° to 68° C.). The KF at which the cloud point occurred was 1.90% and the amount of cyclohexane slurry used to reach the cloud point was 6.2 kg. The batch was then cooled to 60° C. and seeded with 400 g of finely-milled K-salt and aged at reflux (70° C.) for one hour. Cyclohexane (24.9 kg) which had been heated to 65° C. was added to the batch over 1 hour. During this addition, the batch was maintained at reflux. After the addition, the batch KF was 1.21%. The batch was distilled at constant volume with simultaneous addition of 35 kg of 75:25 cyclohexane:isopropanol to achieve a batch KF of 0.54%. Eleven gallons of distillate were collected with addition of 6 kg of cyclohexane to the batch during the concentration step. The KF at the end of this concentration was 0.11%. After cooling to 20°–25° C., the batch was filtered on a 19" filter pot set with cloth-paper-cloth and filtered under a nitrogen atmosphere. The cake was washed with 20 kg of 75:25 cyclohexane:isopropanol followed by 20 kg of CH. The batch was dried on trays at 45°–50° C. under vacuum.

EXAMPLE 3
2-n-butyl-4-chloro-1-[(2'-(tetrazol-5-yl)-1,1'-biphenyl-4-yl)-methyl]-1H-imidazole-5-methanol potassium salt 25.5 kg of isopropanol, 940 ml of deionized water and 8.0 kg of K-salt were charged to a 50 gallon vessel. The KF of the solution was 2.69%. In a 20 gallon vessel, 12.4 kg of cyclohexane and 40 g of alpine milled K-salt seed was heated to 57° C. The batch in a 50 gallon vessel was heated to reflux (82° C.) and the cyclohexane slurry was added to it over a period of 1 hour 10 minutes. During the addition, the batch was maintained at reflux (the reflux temperature dropped from 82° C. to 72° C. during this addition). The KF at the cloud point was 2.1%, and 400 g of finely-milled K-salt seed was added and aged at reflux for 2 hours (69° C.). The amount of cyclohexane slurry added to attain the cloud point was 10.4 kg. After the age, an additional 20.7 kg of cyclohexane was added to the batch over 1 hour while maintaining the batch temperature at 65° C. The KF at the end of the cyclohexane addition was 1.39%. The batch was distilled at constant volume with 73 kg of 75:25 cyclohexane:isopropanol to a KF of 0.23% followed by a concentration to half volume (15 gallons of distillate collected with 7.5 kg of cyclohexane added). No water was detected at the end of the concentration. The batch was cooled to 20°–30° C., filtered and washed, as before with 20 kg of 75:25 cyclohexane:isopropanol followed by 20 kg of CH. HPLC wt % was 99.5%, area %=99.9%. The KF was 0.3%.

EXAMPLE 4
2-n-butyl-4-chloro-1-[(2'-(tetrazol-5-yl)-1,1'-biphenyl-4-yl)-methyl]-1H-imidazole-5-methanol potassium salt 25.4 kg of isopropanol, 1000 ml of deionized water, and 8.00 kg of K-salt were charged to a 50 gallon vessel. Since the KF was 3.15%, the batch was distilled at constant volume with the concomitant addition of 4.1 L of isopropanol to attain a KF of 2.73%. 12.4 kg of cyclohexane and 40 g of finely milled K-salt seed were charged to a 20 gallon vessel and heated to 55° C. The slurry was added to the batch over a period of 2 hours while maintaining the batch temperature at 70° C.

Turbidity was noted as early in the cyclohexane slurry addition as KF=2.4%. However, the batch was seeded at a KF of 2.25%. The amount of slurry added to achieve this KF was 9.9 kg. The batch was aged for two hours at 68° C. At the end of the age, the seed appeared to have dissolved.

Five liters of cyclohexane containing 25 g of finely-milled K-salt seed was added at room temperature over a period of one minute via the subsurface line to the crystallizer. The temperature of the batch dropped from 68° to 64° C. during this addition. The batch KF was 1.93%. After a 10 minute age, 400 g of finely-milled K-salt seed was added, the batch was aged for two hours at 69° C., and 21.2 kg of cyclohexane (at 62° C.) was charged over 1 hour while maintaining the batch temperature at 68° C. The KF was 1.23%. The batch was distilled at constant volume with the addition of 42 kg of 75:25 cyclohexane:isopropanol (15 gal of distillate collected). The KF was 0.4%. The batch was then concentrated to half volume with the addition of 6 kg of cyclohexane (15 gal of distillate collected). The KF was 0.14%. Finally, to further reduce the KF, an additional 15 gal of distillate was collected with the simultaneous addition of 45 kg of 75:25 cyclohexane:isopropanol to a final KF of 0.02%. The batch was filtered on the 19" filter pot, washed with 20 kg of 75:25 cyclohexane:isopropanol and 20 kg of cyclohexane, and dried under vacuum at 45°–50° C. A total of 7.59 kg of material was produced having a purity of 99.3 wt %, 99.9 area % and a KF of 0.2%.

EXAMPLE 5
2-n-butyl-4-chloro-1-[(2'-(tetrazol-5-yl)-1,1'-biphenyl-4-yl)-methyl]-1H-imidazole-5-methanol potassium salt In a 50 gallon vessel, 25.4 kg of isopropanol, 1044 ml of water and 8.0 kg of K-salt were charged. The KF was 2.61%. 12.4 kg of cyclohexane along with 40 g of finely-milled K-salt seed to a 20 gallon vessel and heated to about 73° C. The cyclohexane slurry was added over 45 minutes.

The batch temperature started out at 73° C. and dropped to 70° C. during the transfer. The cyclohexane temperature was 55° C.

After a 10 minute age, 400 g of finely-milled K-salt was added. The batch was aged for 2 hours while maintaining the temperature at 60°–65° C. 18.7 kg of cyclohexane, heated to 65° C., was charged to the batch over 70 minutes while maintaining the batch at 64° C. The KF at the end of the addition was 1.36%. The batch was distilled at constant volume with concomitant addition of 65 kg of 75:25 cyclohexane:isopropanol (19 gal of distillate was collected). The KF was 0.51%. The batch was then concentrated to half volume as in previous batches and the final KF was 0.02%. The batch was filtered, washed, and dried as before, and then milled at low speed and blended. 7.4 kg of K-salt was produced with 99.9 wt % purity, 99.9 area % purity, and KF of 0.1%.

What is claimed is:

1. A process for the crystallization of losartan potassium comprising the steps of:

a) distilling an isopropanol-water mixture containing losartan potassium to about 2.4 to about 2.8% water content;

b) cooling the mixture to between about 65° and about 70° C.;

c) adding about a 0.5% by weight finely-milled losartan potassium in cyclohexane slurry at between about 60° and about 65° C. at a rate of about 0.3 l/min. to the vessel until the cloud point is reached at about 1.8 to about 2.3% water content;

d) aging the mixture for about ten minutes;

e) adding about 3 to about 10% by weight finely-milled losartan potassium to seed the mixture at a temperature range of about 60° C. to about 70° C.;

f) aging the seeded mixture for about 1 to about 2 hours at a temperature range of about 60° C. to reflux while stirring;

g) adding about a 60°–65° C. solution of cyclohexane over about a two hour period maintaining a temperature of about 68° C. for the mixture;

h) distilling the mixture at a constant volume to a water content of about 0.5%, while maintaining the constant volume by addition of between about a 50:50 and a 80:20 volume to volume ratio of cyclohexane and isopropanol;

i) distilling the mixture to a slurry density of about 200 g/l and a water content of about less than 0.1%, while adding cyclohexane to maintain about a volume to volume ratio of between about a 50:50 to about a 60:40 cyclohexane: isopropanol, if necessary;

j) cooling the mixture to between about 20° C. and about 30° C.;

k) filtering the mixture to isolate the crystalline losartan potassium;

l) washing the crystalline material with 75:25 cyclohexane: isopropanol;

m) washing the crystalline material with cyclohexane; and n) drying the crystalline losartan potassium under vacuum at a temperature of about 45° to about 50° C.

TABLE 1

Comparison of Process Parameter for Examples 1–5

| Process Parameter | Example 1 | Example 2 | Example 3 | Example 4 | Example 5 |
|---|---|---|---|---|---|
| starting KF | 2.64% | 2.48% | 2.69% | 2.73% | 2.61% |
| KF at cloud | 1.94% | 1.90% | 2.10% | 2.25%, 1.93%* | 2.00% |
| temp at seeding | 68° C. | 60° C. | 70° C. | 65–70° C. | 65–70° C. |
| rpm after seeding | 90 | 125 | 90 | 90 | 90 |
| age time | 2 hours | 1 hour | 2 hour | 2 hours | 2 hours |
| temp. | 68° C. | reflux | 65° C. | 69° C. | 60–65° C. |
| KF after CH added | 1.20% | 1.21% | 1.39% | 1.28% | 1.36% |
| CVD time | 1.25 hour | 1 hour | 1 hour | 1.5 hours | 2 hours |
| end KF | 0.24% | 0.54% | 0.23% | 0.4% | 0.51% |
| conc time | 1 hours | 45 min | 45 min | 1 hour | NA |
| KF | 0.02% | 0.11% | 0.0% | 0.02% | 0.02% |

*The 5% seed dissolved at the first KF. Additional 0.5% seeded cyclohexane was added at room temperature to reach the second KF and 5% seed was added.
CVD = constant volume distillation
KF = Karl Fischer determination of water content 2. The process as recited in claim 1, wherein about 3 to about 8% by weight finely-milled losartan potassium is added.

3. The process as recited in claim 2 wherein the the isopropanol-water distillation step is run until about 2.6 to about 2.8% water content is reached.

4. The process as recited in claim 3 wherein the cyclohexane-losartan potassium slurry until the cloud point is reached at about 1.8 to about 2.0% water content.

5. The process as recited in claim 4 wherein the temperature during the seed step is about 65° to about 70° C.

6. The process as recited in claim 5 wherein the constant volume distillation is conducted until the water content is about 0.5%.

7. The process as recited in claim 6 wherein about 5% by weight finely-milled losartan potassium is added.

8. The process as recited in claim 7 wherein the particle size of the finely-milled losartan potassium is about 8 to about 10 $\mu$m.

* * * * *

UNITED STATES PATENT AND TRADEMARK OFFICE
CERTIFICATE OF CORRECTION

PATENT NO. : 5,859,258

DATED : 1/12/99

INVENTOR(S) : Patrick Breen, Erik A. Dienemann, Albert D. Epstein, Karen A. Larson, Michael T. Kennedy, Hari Mahadevan It is certified that error appears in the above-identified patent and that said Letters Patent is hereby corrected as shown below:

On the cover page : Item [54] and column 1, line 3 should read as follows:

PROCESS FOR THE CRYSTALLIZATION OF LOSARTAN

Signed and Sealed this

Eighth Day of June, 1999

Attest:

Attesting Officer

Q. TODD DICKINSON

Acting Commissioner of Patents and Trademarks